July 9, 1946. J. H. KLUIS ET AL Plant Pat. 707

ROSE PLANT

Filed May 21, 1942

WITNESS

Addison E. Avery

INVENTORS
JOHAN HENDRIK KLUIS
ANTHONY KLUIS

BY John H. Rauch Jr.
ATTORNEY

Patented July 9, 1946

UNITED STATES PATENT OFFICE

707

ROSE PLANT

Johan Hendrik Kluis and Anthony Kluis, Boskoop, Netherlands; vested in the Alien Property Custodian Application May 21, 1942, Serial No. 443,971

1 Claim. (Cl. 47—61)

Figures 1, 2:
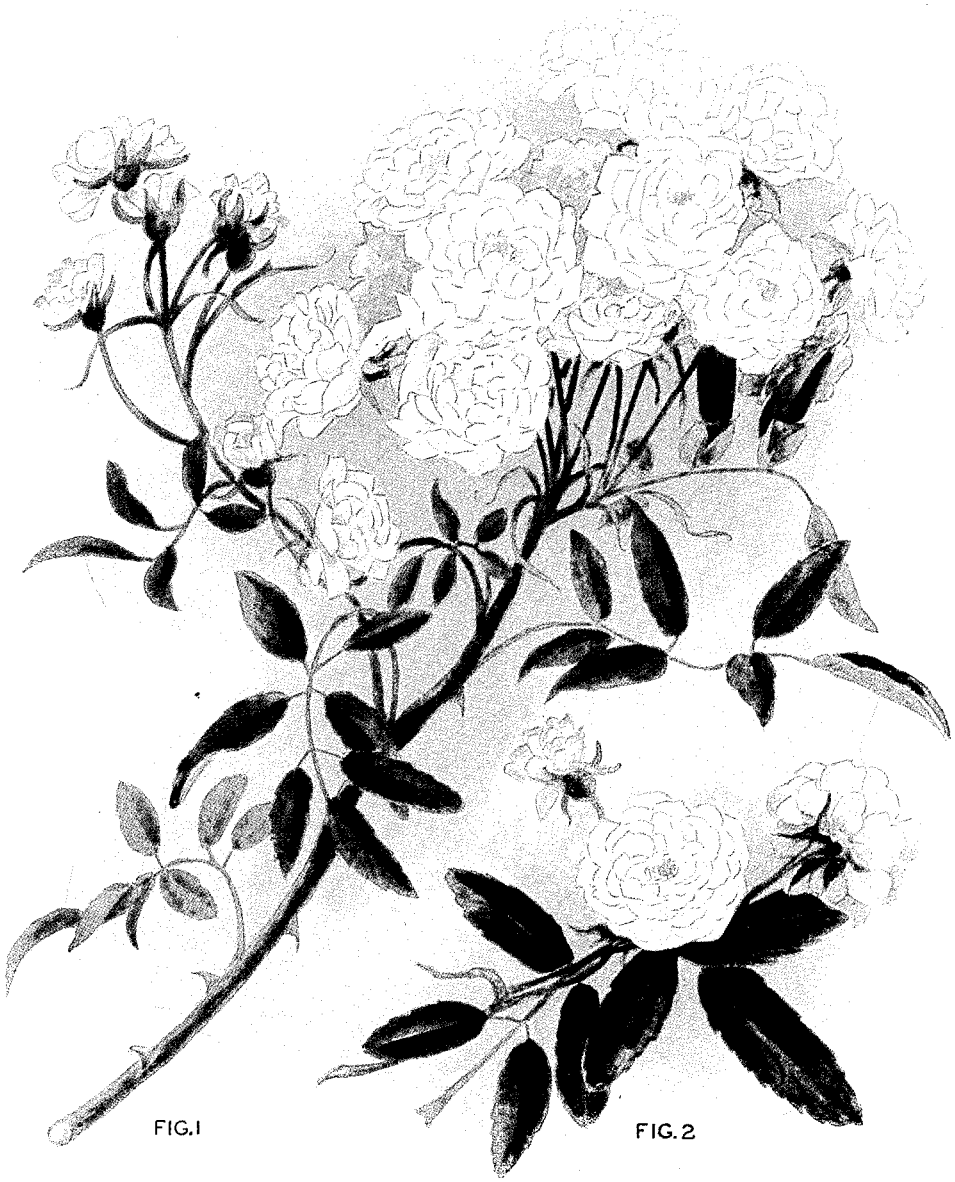

This invention relates to a new variety of rose, a *Rosa polyantha* which is a sport of the Polyantha Rosa Marieanna Kluis Superior, the Polyantha Rosa Marieanna Kluis Superior being a sport of the rose Polyantha Louise Walter.

The new rose was first developed by Johan Hendrik Kluis in his nursery at Boskoop, in the Kingdom of Netherlands, in 1934, by careful selection of specimens of the Polyantha Rosa Marieanna Kluis Superior and propagation thereof by Johan Hendrik Kluis, during which the present sport appeared. The plant has been reproduced asexually in considerable quantities.

The plant is a dwarf and of a strong growth, reaching a height of about eighteen inches with an average spread of about fifteen inches. It is hardy and flowers from May until November, or usually until the first snow of the fall or winter season. The plant is above average in resistance to disease and is exceptionally resistant to mildew.

The foliage is closely set and glabrous, the full grown leaves generally being green, comparable to Maerz & Paul Plate No. 24–J–7, on the upper surface and a lighter green, comparable to Holly Green, Maerz & Paul Plate No. 23–L–1, on the under surface. The new leaves are a lighter green.

The plant is almost thornless, the occasional thorns being unevenly distributed and of a color comparable to Maerz & Paul Plate No. 22–H–1. They have relatively wide bases with medium long points which curve downwardly.

The flowers are from one to one and one-half inches in diameter and are borne in clusters of four to six on terminals of the main stalk and on strong laterals. The flowers average under normal conditions about thirty-five to forty-five petals each.

The stems are stiff, slender and generally upright and support the flowers well. They are of a color comparable to Biscay Green, Maerz & Paul Plate No. 21–K–5.

The flowers have good lasting qualities and the persistence of the petals on the flowers is above average. The color is uniform and of lasting quality both on the plant and as a cut flower. The flower has the appearance of being uniform in color throughout its extent but examination of the petals discloses differences in color at various portions of the flower. The base of the petals is green with a tinge of yellow, comparable to Maerz & Paul Plate 18–E–1. The central portions of the petals are Geranium Pink or Bermuda, comparable to Maerz & Paul Plate No. 1–J–8, the outer edges being a color comparable to Maerz & Paul Plate 1–K–11, but somewhat more intense. The deeper tone in the shadowpits of the petals is comparable to Maerz & Paul Plate 2–L–8. The tips of the bud petals are of a color comparable to Maerz & Paul Plate No. 5–K–4.

The drawing and the following tabulation further illustrate and describe the characteristics of the variety:

*General*

Parentage: The plant is a sport of Polyantha Rosa Marieanna Kluis Superior which is a sport of the Polyantha Rosa Louise Walter.

*Flower*

Blooming habit: Location where observations were made—trial field of Gerard K. Klyn, Mentor, Ohio, and in the trial field of Johan Hendrik Kluis, in Boskoop, Netherlands.

*Flowering.*—May to November, usually until the first snow of the fall and winter season.

Asexual reproduction: Budding in summer, grafting in winter.

Bud:

*Size.*—Small.

*Form.*—Semi-globular.

*Color.*—When sepals first divide—comparable to Maerz & Paul Plate No. 5–K–4. When petals begin to unfurl—Red with Yellow over-cast, comparable to Maerz & Paul Plate No. 2–K–11. When half blown—Copperish-Orange, comparable to Maerz & Paul Plate No. 2–L–8.

*Sepals.*—Regular, smooth, narrow, elongated, pointed, recurvant, light yellowish green.

*Calyx.*—Shape—segmental, smooth, light yellowish green. Size—very small. Aspect—smooth and serrated. Aroma when rubbed—none.

*Peduncle.*—Length—about one and one-half to two and one-half inches. Aspect—rounded and smooth. Color—light yellowish green, sometimes with brownish cast near base. Strength—ample, well proportioned to bloom and holds flowers generally upright without pendancy. Opening—opens well in blooming season regardless of weather conditions.

Bloom:

*Size.*—Small, one to one and a half inches.

*Borne.*—Mostly in clusters of four to six on terminals of main stalk and on strong laterals.

*Stems.*—Stiff, slender, and generally upright.

*Form.*—When first opened, cup shaped.

*Permanence.*—Good until ready to shed.

Petalage: Number of petals under normal conditions, thirty-five to forty-five.

*Color.*—Center of flower—shades from Geranium Pink or Bermuda, Maerz & Paul Plate No. 1–J–8 to Maerz & Paul Plate No. 2–L–8. Outer petals—same. Base of petals—Green with a tinge of Yellow, Maerz & Paul Plate No. 18–E–1. Inside of petals—center, Geranium Pink or Bermuda, Maerz & Paul Plate No. 1–J–8. Outer edge—Maerz & Paul Plate No. 1–K–11, but more intense. Reverse of petals—about the same as inside. General tonality from a distance—comparable to Flamingo, Maerz & Paul Plate No. 2–I–11.

*Variegations.*—Uniform or none.

*Discoloration.*—General tonality remains constant from first day until the end.

Petals:

*Texture.*—Medium thickness.

*Form.*—Shell shaped, concave upwardly with curvant margins.

*Arrangement.*—Imbricated.

*Petaloids in center.*—Few.

*Persistence.*—On bloom—above average.

*Fragrance.*—None.

*Nature.*—Slight.

*Lasting quality.*—On plant—good. As a cut flower—good.

Genital organs:

*Stamens.*—Normal in quantity and size and of medium length.

*Color.*—Yellow.

*Arrangement.*—Normal and regular.

*Pollen.*—Golden Rod Yellow, Maerz & Paul Plate No. 10–L–5.

*Styles.*—Light yellowish green, medium to normal in size, shape, and arrangement.

*Stigmas.*—Light yellow and of average size and shape.

*Ovaries.*—Semi-globular.

Fruit:

*Form.*—Semi-globular, medium in size.

*Aspect.*—Smooth.

*Color at maturity.*—Reddish.

*Sepals.*—Average.

*Plant*

Form: A dwarf.

Growth: Strong, to a height of eighteen inches with average spread of fifteen inches.

Foliage: Closely set and glabrous, with seven leaflets.

*Size.*—Medium.

*Quantity.*—Ample.

*Color.*—Upper side—Green comparable to Maerz & Paul Plate 24–J–7; under side—Holly Green, Maerz & Paul Plate No. 23–L–1.

*Shape.*—Normal; somewhat lenticular and elongated.

*Texture.*—Upper side—smooth with ribs depressed. Under side—smooth but ribs ridged. Ribs and veins—same color, nor-normal and average.

*Edges.*—Serrated, serrations regular.

*Rachis.*—Generally round and smooth, slightly flattened on upper surface and without prickles.

*Stipules.*—None.

*Disease resistance.*—Above average, exceptionally resistant to mildew.

Wood:

*New wood.*—Color—light green. Bark—light green, smooth.

*Old wood.*—Color—Biscay Green, comparable to Maerz & Paul Plate No. 21–K–5.

Thorns: Practically thornless, but a few irregularly distributed thorns which are comparable to Maerz & Paul Plate No. 22–H–1, in color.

Having now fully shown and described our new rose and mode of its production, what we claim and desire to secure by Letters Patent of the United States is:

The new variety of rose plant herein shown and described, characterized predominantly by the unusual color of the flowers.

JOHAN HENDRIK KLUIS.
ANTHONY KLUIS.